US009629589B2

(12) United States Patent
Demianovich et al.

(10) Patent No.: US 9,629,589 B2
(45) Date of Patent: Apr. 25, 2017

(54) MOVING A COMPONENT OF AN IMAGING SYSTEM

(71) Applicant: General Electric Company, Schenectady, NY (US)

(72) Inventors: Nicholas Demianovich, Waukesha, WI (US); Daniel Alvin Kleewein, Pewaukee, WI (US); Haley Boyd, Laurel, MD (US); Logan Rose, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 321 days.

(21) Appl. No.: 14/465,547

(22) Filed: Aug. 21, 2014

(65) Prior Publication Data

US 2016/0051208 A1 Feb. 25, 2016

(51) Int. Cl.
*A61B 6/00* (2006.01)
*A61B 6/04* (2006.01)
*A61B 6/03* (2006.01)

(52) U.S. Cl.
CPC ............ *A61B 6/0407* (2013.01); *A61B 6/035* (2013.01)

(58) Field of Classification Search
CPC ....... A61B 6/04; A61B 6/0414; A61B 6/0407; A61B 6/0421; A61B 6/0457; A61B 6/508; A61B 6/0435; A61B 5/704
See application file for complete search history.

(56) References Cited

U.S. PATENT DOCUMENTS

| 7,108,421 | B2 * | 9/2006 | Gregerson | ............ | A61B 6/032 |
| | | | | | 378/146 |
| 8,258,190 | B2 | 9/2012 | Skaff et al. | | |
| 8,505,959 | B2 | 8/2013 | Darling, III et al. | | |
| 2014/0155753 | A1 | 6/2014 | McGuire, Jr. et al. | | |

OTHER PUBLICATIONS

Prior Art Photograph, dated Oct. 25, 2013, submitted by the inventor, no further information available.

* cited by examiner

*Primary Examiner* — Hoon Song
(74) *Attorney, Agent, or Firm* — Fletcher Yoder, P.C.

(57) ABSTRACT

Techniques for moving a component of an imaging system are described herein. The techniques may include an apparatus having a component bracket to attach to an imaging system component disposed within a gantry of the imaging system. The apparatus may include a platform bracket to attach to a movable platform of the imaging system, wherein the component bracket and the platform bracket are to be coupled to each other.

21 Claims, 9 Drawing Sheets

200

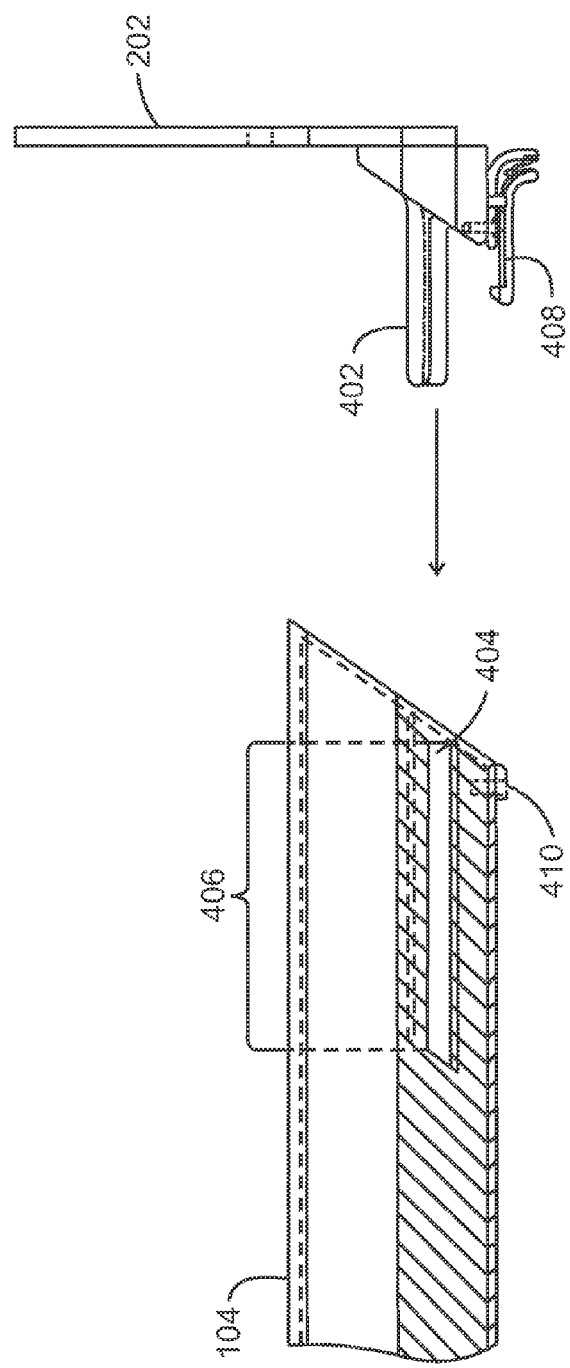
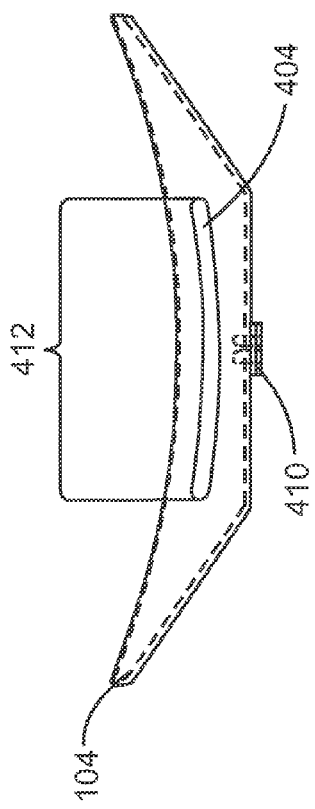
FIG. 4A
FIG. 4B

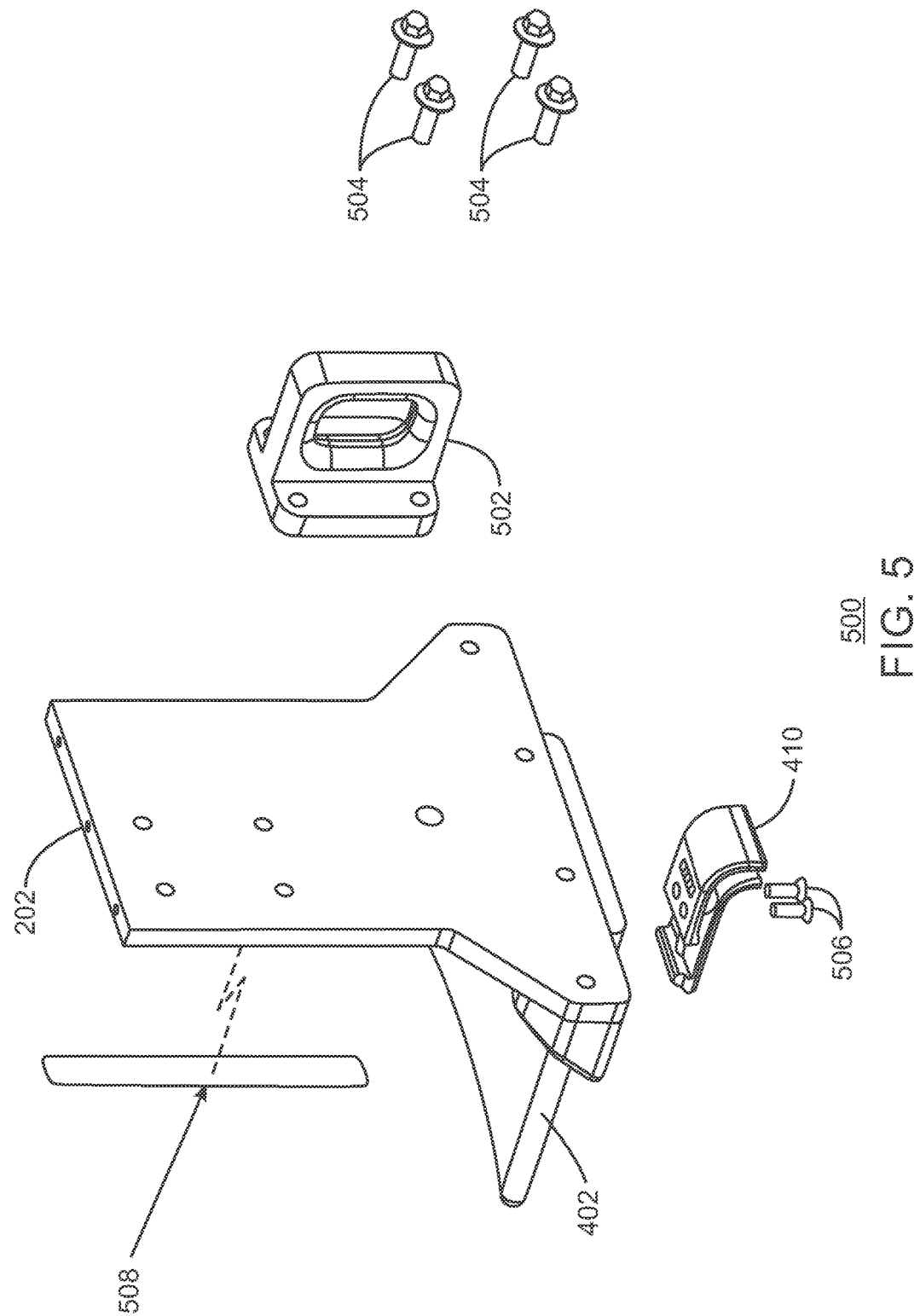

800

MOVING A COMPONENT OF AN IMAGING SYSTEM

BACKGROUND OF THE INVENTION

The subject matter disclosed herein relates generally to techniques for movement of a component of an imaging system. In a medical imaging system, such as in an x-ray computed tomography (x-ray CT) imaging system, a subject may be placed on an imaging platform such as a bed, or other platform configured to pass through a gantry. The gantry may define an opening referred to as a bore. As the subject, such as a patient moves through the bore, components within the gantry emit radiation. The gantry may include other components, such as a collimator configured to narrow radiation beams, or otherwise adjust radiation slice thickness. The components that are disposed within the gantry may be difficult to service. In some scenarios, a component disposed within the gantry may be required to be lifted out of the gantry for servicing, repair, and/or replacement. However, removing components from the gantry is challenging due to the weight of the components, obstruction caused by the gantry itself, and the like. In some circumstances, cranes have been developed to assist in removing components of the imaging system, yet servicing components of the gantry remains difficult.

BRIEF DESCRIPTION OF THE INVENTION

An embodiment relates to an apparatus for moving a component of an imaging system. The apparatus includes a component bracket to attach to an imaging system component disposed within a gantry of the imaging system. The apparatus includes a platform bracket configured to attach to a movable imaging platform of the imaging system. The component bracket and the platform bracket are configured to be coupled to the each other.

Another embodiment relates to a method for moving a component of an imaging system. The method includes attaching a component bracket to an imaging system component disposed within a gantry of the imaging system. The method also includes attaching a platform bracket to a movable imaging platform of the imaging system. The method further includes coupling the component bracket and the platform bracket to each other.

Still another embodiment relates to a system for moving a component of an imaging system. The system includes a component bracket to attach to an imaging system component. The imaging system component is disposed within a gantry of the imaging system. The system also includes a platform bracket to attach to a movable imaging platform of the imaging system. The system further includes a winch to couple the component bracket to the platform bracket.

BRIEF DESCRIPTION OF THE DRAWINGS

The present techniques will become more fully understood from the following detailed description, taken in conjunction with the accompanying drawings, wherein like reference numerals refer to like parts, in which:

FIG. 4A is a diagram illustrating a side view of a platform bracket to be received at an imaging platform;

FIG. 4B is a diagram illustrating is a back view of an imaging platform having a recess to receive a platform bracket;

FIG. 5 is a diagram illustrating an expanded perspective view of a platform bracket and additional elements to be attached to the platform bracket;

DETAILED DESCRIPTION OF THE INVENTION

In the following detailed description, reference is made to the accompanying drawings that form a part hereof, and in which is shown by way of illustration of specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the embodiments described herein.

Various embodiments provide techniques for moving a component of an imaging system. For example, a collimator may be disposed within a gantry of an imaging system. As discussed above, servicing such a component may be difficult. The embodiments described herein utilize a component bracket to attach to the imaging system component, and a platform bracket to attach to a movable platform of the imaging system. A platform bracket, as referred to herein, is a component configured to attach to a movable platform of the imaging device, such as a movable bed of a medical imaging device. Further, the platform bracket is attachable to the component of the imaging system, or to a component bracket that is attachable to the component, such as a collimator of a medical imaging system. The platform bracket may be attachable, in some cases, by being received into a cavity or opening of the movable platform. In some cases, the platform bracket may be a modified bracket typically used for phantom object testing. In this scenario, the platform bracket may include some type of hanger, or attachment mechanism to be coupled to the medical imaging system component. The movable platform may be, in some cases, a bed upon which a subject is typically placed for medical imaging of the subject. The techniques described herein utilize the movability of the imaging platform to move, and in scenarios remove, components from the gantry of a given imaging system.

Figure 1:
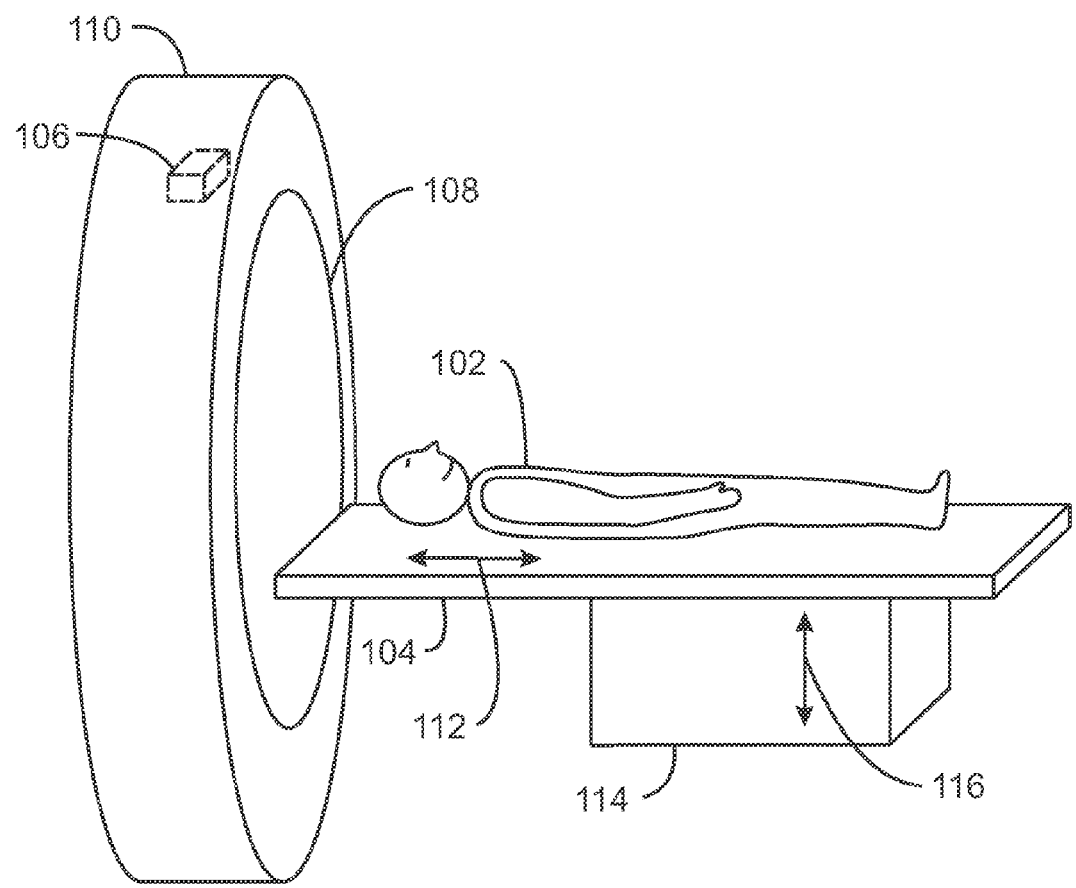
FIG. 1 illustrates a diagram of a medical imaging system.

FIG. 1 illustrates a diagram of a medical imaging system. In the imaging system 100, a subject 102 can be a human patient in one embodiment. It should be noted that the subject 102 does not have to be human. In embodiments, the subject is some other living creature or inanimate object. Whether the subject 102 is a human, an animal, or some other inanimate object is immaterial to the present disclosure. In general, the present disclosure utilizes an imaging platform 104 that is typically used to place the subject 102 to remove an imaging component, indicated at the dashed box 106.

As illustrated in FIG. 1, the subject 102 can be placed on the imaging platform 104 that can move a subject horizontally for locating the subject 102 in the most advantageous imaging position within a bore 108 of a gantry 110, as indicated at 112. A bed mechanism 114 can raise and lower the imaging platform 104 vertically for locating the subject in the most advantageous imaging position, as indicated at 116.

Although the imaging component 106 is illustrated as being disposed at a top portion of the gantry 110, in embodiments, the gantry 110 may be configured to rotate such that the imaging component 106 may be disposed at a bottom portion of the gantry 110. This enables the imaging platform 104 to be used as a lifting and moving mechanism when the imaging component 106 is in need of regular or necessary service.

Although not illustrated in FIG. 1, the imaging platform 104 may be used to remove the imaging component 106 within the gantry 110. As discussed in more detail below, a bracket may attach to the imaging component 106 and be coupled to a platform bracket that is to be received at the imaging platform 104. This arrangement enables a service technician to utilize the imaging platform 104 as a lifting and traversing mechanism.

Further, although the gantry 110 is shown as circular in one embodiment. In other embodiments the gantry 110 may be of any shape such as square, oval, "C" shape, a hexagonal shape, and the like. Further, the system described herein for moving imaging components may be used in any sort of imaging system, not necessarily the imaging system illustrated in FIG. 1. Other systems, wherein an imaging platform is configured with the capacity to raise and lower an imaging subject 102 may incorporate the techniques described herein wherein attachments to the imaging platform are used to raise, lower, and horizontally move an imaging component.

The block diagram of FIG. 1 is not intended to indicate that the imaging system 100 is to include all of the components shown in FIG. 1. Further, the imaging system 100 may include any number of additional components not shown in FIG. 1, depending on the details of the specific implementation.

Figure 2:
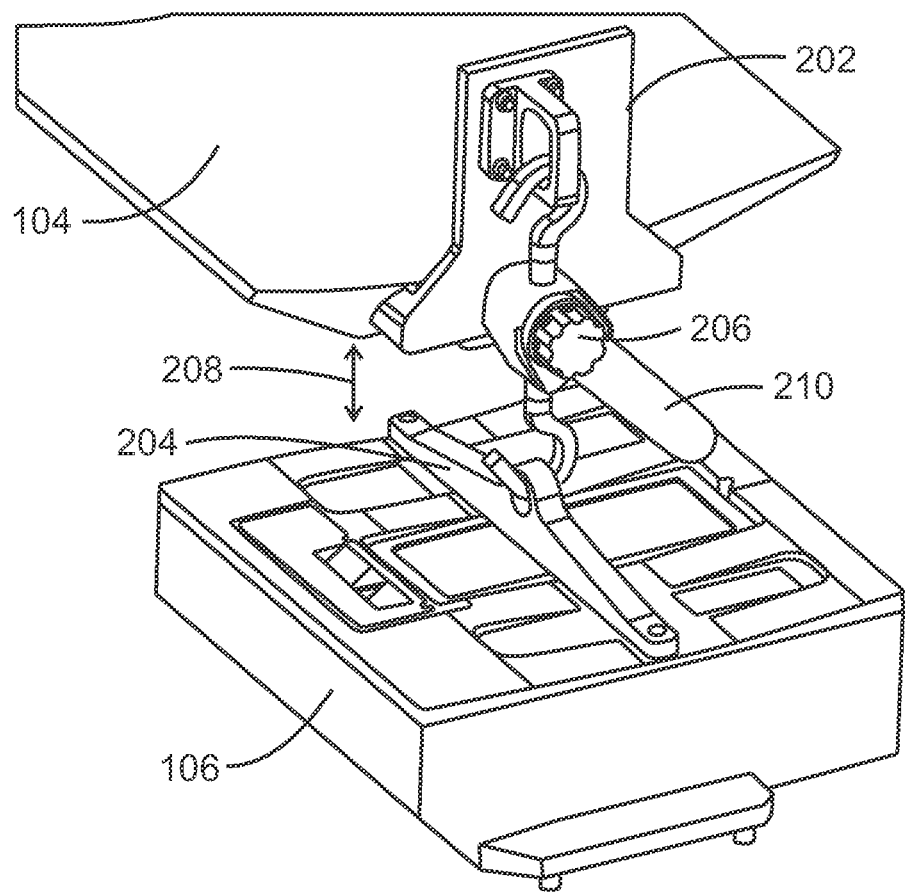
FIG. 2 illustrates a perspective view of a diagram of an example system for moving an imaging system component.

FIG. 2 illustrates a perspective view of a diagram of an example system for moving an imaging system component. The system 200 includes a platform bracket 202 and a component bracket 204. An imaging component, such as the imaging component of FIG. 1, is configured to be disposed within the gantry 110 of FIG. 1. In the example illustrated in FIG. 2, the imaging component 106 is a collimator. However, the techniques described herein are applicable to moving other components typically disposed within a gantry, such as the gantry 110 of the imaging system 100.

As illustrated in FIG. 2, the component bracket 204 is configured to be attached to the imaging component 106. The platform bracket 202 is configured to be attached to an imaging platform, such as the imaging platform 104 of FIG. 1. As discussed in more detail below, the platform bracket 202 may include a protrusion to be received by an opening defined by the imaging platform 104.

The component bracket 204 may be coupled to the platform bracket 202. In one scenario, the component bracket 204 and the platform bracket may be coupled by a winch 206. The winch 206 is configured to be extendable and retractable, as indicated by the arrow 208. In some embodiments, the winch 206 may include an arm 210 to enable manual extension and/or retraction of the winch 206. While the imaging platform 104 may able to travel the direction 208, in some scenarios, the gantry 110 may impede vertical movement of the imaging platform 104. In this scenario, the imaging component 106 may be lowered by winch 206 onto a servicing cart (not shown) at the back of the gantry after moving the imaging component 106 through the gantry 110. The winch 206, therefore, extends vertical movement of the system 200 in cases where the gantry 110 vertically lowering the imaging component 106. As discussed in more detail below, other arrangements of the system 200 are contemplated.

Figure 3A:
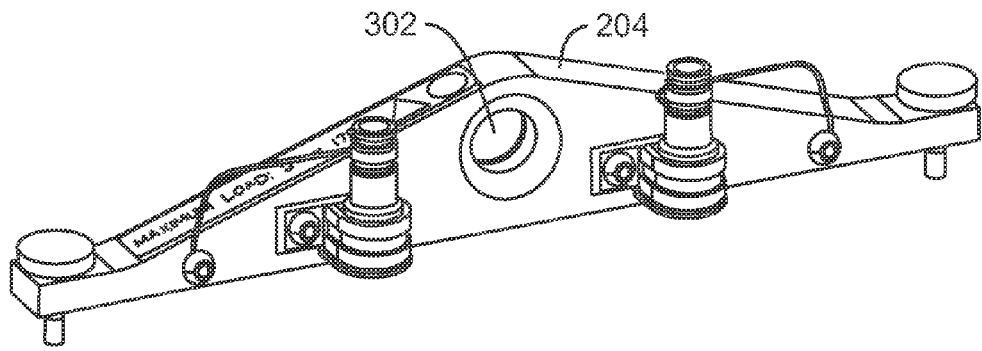
FIG. 3A is a perspective view of a diagram illustrating a component bracket.

FIG. 3A is a perspective view of a diagram illustrating a component bracket. The component bracket 204 may define an opening 302. The opening 302 may receive a mechanism, such as a hook of the winch 206 of FIG. 2, to couple the component bracket 204 to the platform bracket 202 discussed above.

Figure 3B:
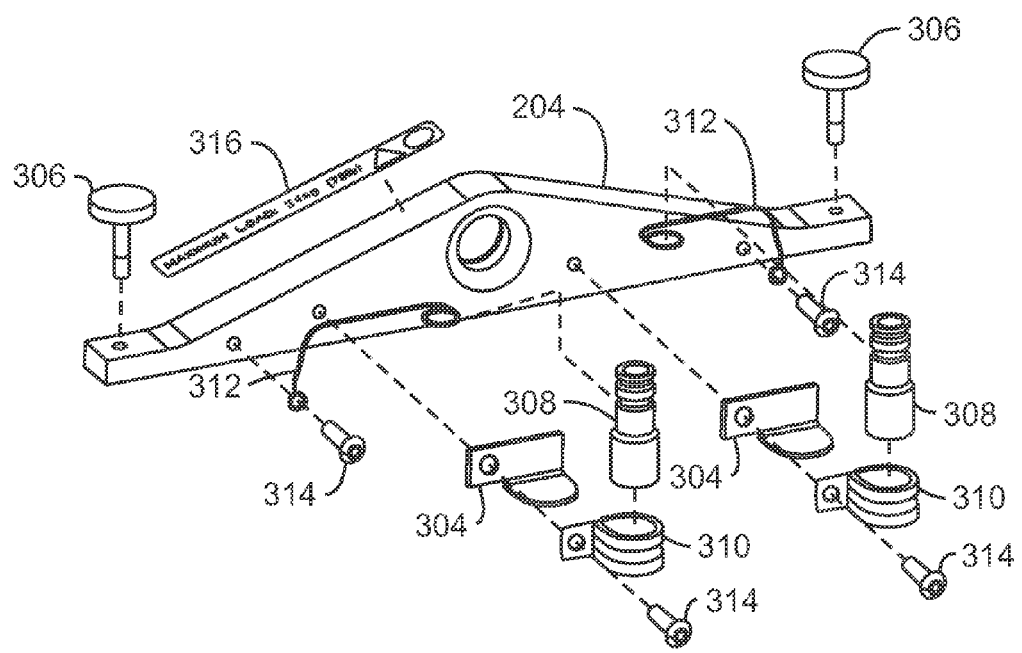
FIG. 3B is a perspective view of a diagram illustrating an expanded view of the component bracket.

FIG. 3B is a perspective view of a diagram illustrating an expanded view of the component bracket. The component bracket 204 may also include stoppers 304, thumbscrews 306, spring pin removal mechanisms 308, clamps 310, steel lanyards 312, and fasteners 314.

FIG. 3A and FIG. 3B illustrate only one example of a component bracket. For illustrative purposes, the elements of the component bracket 204 are described herein. The spring pin removal mechanism 308 may be used to unlock an imaging component, such as the imaging component 106, from various fasteners within the gantry 110. The clamps 310 are configured to hold the spring pin removal mechanisms 308 with fasteners 314 and the stoppers 304. The steel lanyards 312 may prevent loss of the spring pin removal mechanisms 308. The thumbscrews 306 may be manually tightened and loosed to attach the component bracket 204 to the imaging component 106.

In some embodiments, the component bracket 204 may also include a load rating sticker 316. The load rating sticker 316 may be useful for a technician to gauge whether an imaging platform, such as the imaging platform 104 of FIG. 1, has the capacity to lift the imaging component 106 without damaging the imaging component 106, the movement system, such as the system 200 of FIG. 2, or the imaging platform 104.

FIG. 4A is a diagram illustrating a side view of a platform bracket to be received at an imaging platform. The platform bracket 202 includes a protrusion 402 to be received at an opening 404 defined by the imaging platform 104. The length of the protrusion 402 may be equal to, or less than, the depth 406 of the opening 404. In embodiments, the platform bracket 202 may also include a clip 408. The clip 408 may be a spring loaded clip, or other manual release fastening mechanism configured to be received at a retention protrusion 410 of the imaging platform 104. As illustrated in FIG. 4A, the platform bracket 202 may be received within the opening 404 and retained by the combination of the clip 408 and the retention protrusion 410.

FIG. 4B is a diagram illustrating is a back view of an imaging platform having a recess to receive a platform bracket. In this view, the opening 404 along with the retention protrusion 410 of the imaging platform 104 are illustrated as an example. Further, the width 412 of the opening 404 is shown. In embodiments, the protrusion 402 of the platform bracket 202 is at least as wide as the width 412 of the opening 404.

FIG. 5 is a diagram illustrating an expanded perspective view of the platform bracket and additional elements to be attached to the platform bracket. As discussed above in regard to FIG. 4A and FIG. 4B, the platform bracket 202 may include, or may be attached to the protrusion 402. In the example embodiment illustrated in FIG. 5, the platform bracket 202 may be configured to receive a hanger 502 attached to the platform bracket 202 via fasteners 504. Further, a retaining clip, such as the clip 410 of FIG. 4A and FIG. 4B, may be fastened to the platform bracket 202, or to the protrusion 402, via fasteners 506. In some embodiments, the platform bracket 202 may also include a load rating sticker 508 to inform a service technician or other user about load limits for using the platform bracket to lift, or otherwise move, an imaging component, such as the collimator 106 of FIG. 2. The hanger 502 may be configured to receive a hook, or other coupling mechanism, to couple the platform bracket 202 to the component bracket 204. It is important to note that the components, such as the hanger 502, the protrusion 402, the clip 410, may be individual components attached to the platform bracket 202, or may be integrated as a monolithic piece, or may be any combination of monolithic pieces and individual pieces.

Figure 6:
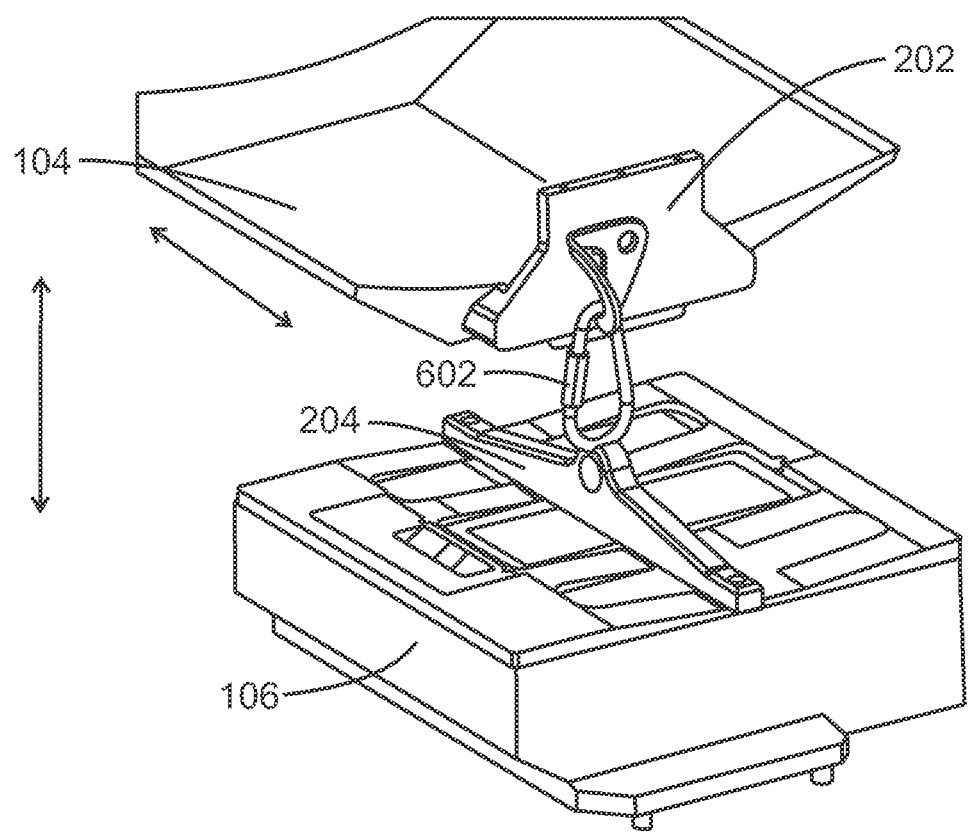
FIG. 6 is a perspective view of an alternative embodiment of an example system for moving an imaging system component.

FIG. 6 is a perspective view of an alternative embodiment of an example system for moving an imaging system component. In FIG. 6, the platform bracket 202 is coupled to the component bracket 204 via a locking metal loop 602. In this example embodiment, a winch, such as the winch 206 of FIG. 2 is not included. Lifting, as well as horizontal movement may still be performed by way of the imaging platform 104 as illustrated in FIG. 6.

Figure 7:
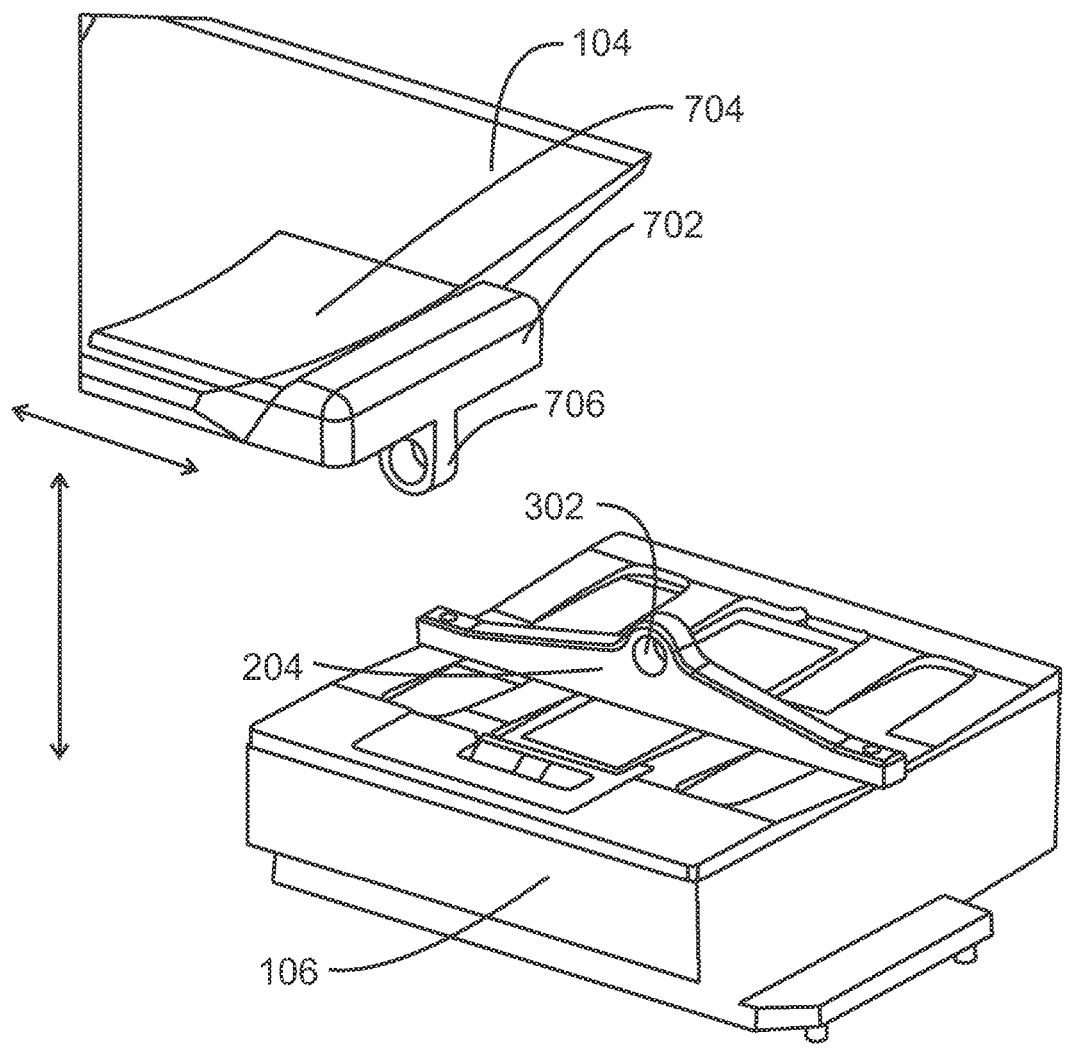
FIG. 7 is a perspective view of another alternative embodiment of an example system for moving an imaging system component.

FIG. 7 is a perspective view of another alternative embodiment of an example system for moving an imaging system component. In FIG. 7, the component bracket 204 is similar to the component bracket illustrated in FIG. 2. However, in this example embodiment, a platform bracket 702 may include a protrusion 704 to be received at the imaging platform 104, as well as a receiver 706. The receiver 706 may be coupled by any suitable fastener, such as the locking metal loop 602 of FIG. 6, a winch, such as the winch 206 of FIG. 2, to an opening, such as the opening 302 described above in regard to FIG. 3 of the component bracket 204.

Figure 8:
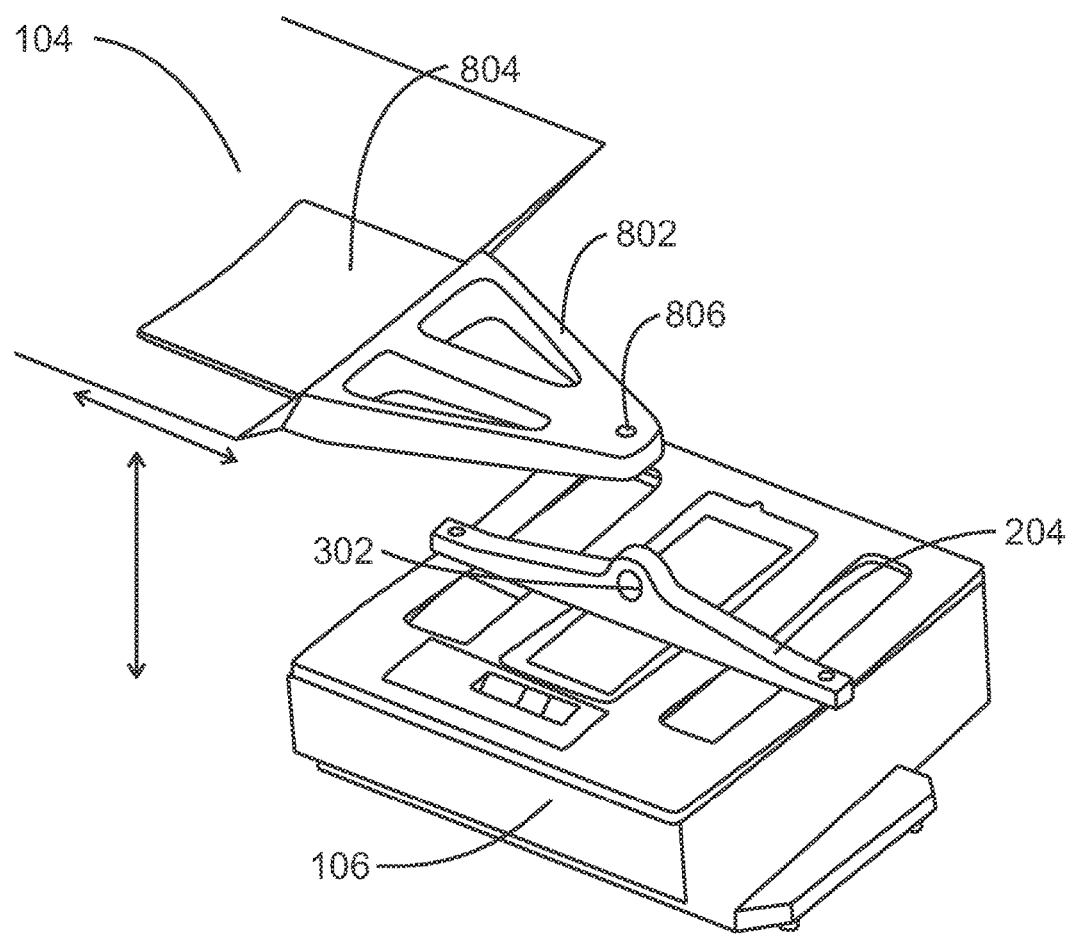
FIG. 8 is a perspective view of yet another alternative embodiment of an example system for moving an imaging system component.

FIG. 8 is a perspective view of yet another alternative embodiment of an example system for moving an imaging system component. In FIG. 8, the component bracket 204 is similar to the component bracket illustrated in FIG. 2. However, in this example embodiment, a platform bracket 802 may include a protrusion 804 to be received at the imaging platform 104, as well as an opening 806 defined by the platform bracket 802. The opening 806 may be coupled by any suitable fastener, such as the locking metal loop 602 of FIG. 6, a winch, such as the winch 206 of FIG. 2, to an opening, such as the opening 302 described above in regard to FIG. 3 of the component bracket 204.

Figure 9:
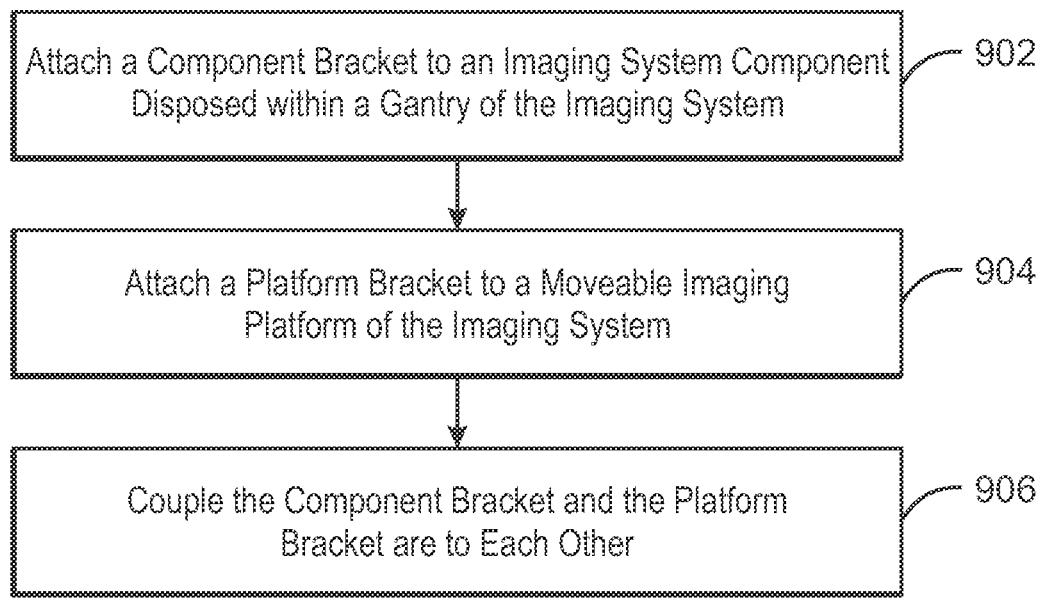
FIG. 9 is a block diagram illustrating a method for moving an imaging system component.

FIG. 9 is a block diagram illustrating a method for moving an imaging system component. The method 900 includes attaching a component bracket to an imaging system component disposed within a gantry of the imaging system at block 902. At block 904, a platform bracket is attached to a movable imaging platform of the imaging system. The component bracket and the platform bracket are coupled to each other at 906.

In some embodiments, the coupling at block 906 is implemented with a winch. The winch may be extendable and retractable. In this embodiment the method may also include extending the winch to lower the imaging system component behind the gantry of the imaging system. This scenario enables the imaging system component to be lowered onto a service crate, for example, when the gantry impedes lowering of the imaging system platform beyond a certain distance.

Attaching the platform bracket at 904 may be done at a side of the imaging platform that is nearest to the gantry. In other words, a side of the imaging platform nearest to the gantry may receive the platform bracket. In some embodiments, the method 900 also includes attaching a hanger to platform bracket and coupling the component bracket to the hanger.

The method 900 may also include raising the imaging system component disposed within the gantry via raising the movable imaging platform. The imaging system component may also be lowered via lowering the movable imaging platform, and moved, in some cases horizontally, or any combination thereof.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the techniques described herein, including the best mode, and also to enable any person skilled in the art to practice the techniques described herein, including making and using any devices or systems and performing any incorporated methods. The patentable scope of the techniques described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for moving a component of an imaging system, comprising:
    a component bracket to attach to an imaging system component disposed within a gantry of the imaging system;
    a platform bracket to attach to a movable imaging platform of the imaging system, wherein the component bracket and the platform bracket are to be coupled to each other; wherein the apparatus is configured to:
    raise the imaging system component disposed within the gantry via raising of the movable imaging platform;
    lower the imaging system component disposed within the gantry via lowering of the movable imaging platform;
    move the imaging system component horizontally; or any combination thereof.

2. The apparatus for moving a component of an imaging system of claim 1, further comprising a winch to couple the component bracket to the platform bracket.

3. The apparatus for moving a component of an imaging system of claim 2, wherein the winch comprises an extendable feature.

4. The apparatus for moving a component of an imaging system of claim 3, wherein the winch comprises an arm to extend and retract the extendable feature.

5. The apparatus for moving a component of an imaging system of claim 1, wherein the imaging platform is a bed for supporting a subject of the imaging system, and wherein the platform bracket is configured to attach to the bed at a side nearest to the gantry of the imaging system.

6. The apparatus for moving a component of an imaging system of claim 1, the platform bracket comprising a protrusion to insert into an opening defined in the imaging platform.

7. The apparatus for moving a component of an imaging system of claim 1, further comprising:
a hanger attachable to the platform bracket; and
fasteners to couple the hanger to the platform bracket.

8. A method for moving a component of an imaging system, comprising:
attaching a component bracket to an imaging system component disposed within a gantry of the imaging system;
attaching a platform bracket to a movable imaging platform of the imaging system;
coupling the component bracket and the platform bracket to each other; and
performing one or more of:
raising the imaging system component disposed within the gantry via raising of the movable imaging platform;
lowering the imaging system component disposed within the gantry via lowering of the movable imaging platform;
moving the imaging system component horizontally; or
any combination thereof.

9. The method for moving a component of an imaging system of claim 8, wherein a winch is used to couple the component bracket to the platform bracket.

10. The method for moving a component of an imaging system of claim 9, wherein the winch comprises an extendable feature.

11. The method for moving a component of an imaging system of claim 10, further comprising:
extending the winch to increase a distance between the component bracket and the platform bracket; and
retracting the winch to decrease distance between the component bracket and the platform bracket.

12. The method for moving a component of an imaging system of claim 8, wherein the imaging platform is a bed for supporting a subject of the imaging system, and wherein attaching the platform bracket to the imaging platform comprises receiving the platform bracket at the imaging platform at a side nearest to the gantry of the imaging system.

13. The method for moving a component of an imaging system of claim 12, wherein receiving the platform bracket at the bed comprises receiving a protrusion of the platform bracket into an opening defined in the imaging platform.

14. The method for moving a component of an imaging system of claim 1, further comprising:
attaching a hanger to the platform bracket; and
coupling the component bracket to the hanger.

15. A system for moving a component of an imaging system, comprising:

a component bracket to attach to an imaging system component disposed within a gantry of the imaging system;
a platform bracket to attach to a movable imaging platform of the imaging system; and
a winch to couple the component bracket to the platform bracket.

16. The system for moving a component of an imaging system of claim 15, wherein the winch comprises:
an extendable feature; and
an arm to extend and retract the extendable feature.

17. The system for moving a component of an imaging system of claim 15, the platform bracket comprising a protrusion to insert into an opening defined in the imaging platform.

18. The system for moving a component of an imaging system of claim 15, wherein the system is configured to:
raise the imaging system component disposed within the gantry via raising of the movable imaging platform;
lower the imaging system component disposed within the gantry via lowering of the movable imaging platform;
move the imaging system component horizontally;
lower the imaging system component via extension of the winch; or
any combination thereof.

19. An apparatus for moving a component of an imaging system, comprising:
a component bracket to attach to an imaging system component disposed within a gantry of the imaging system;
a platform bracket to attach to a movable imaging platform of the imaging system, wherein the component bracket and the platform bracket are coupled to each other by a hanger configured to attach to the platform bracket and fasteners configured to couple the hanger to the platform bracket.

20. A method for moving a component of an imaging system, comprising:
attaching a component bracket to an imaging system component disposed within a gantry of the imaging system;
attaching a platform bracket to a movable imaging platform of the imaging system; and
coupling the component bracket and the platform bracket to each other, wherein a winch is used to couple the component bracket to the platform bracket.

21. A method for moving a component of an imaging system, comprising:
attaching a component bracket to an imaging system component disposed within a gantry of the imaging system;
attaching a platform bracket to a movable imaging platform of the imaging system;
coupling the component bracket and the platform bracket to each other by attaching a hanger to the platform bracket and coupling the component bracket to the hanger.

* * * * *